(12) United States Patent
Doubleday et al.

(10) Patent No.: US 7,240,876 B2
(45) Date of Patent: Jul. 10, 2007

(54) DISPENSER BOX

(75) Inventors: Walter Doubleday, Jupiter, FL (US); Wendy Henderson, Ventura, CA (US); Joseph M. Iglesias, Newbury Park, CA (US); Kenneth Helenbolt, North Hollywood, CA (US); Michael Campos, Sylmar, CA (US); Wendee Lee, West Hills, CA (US); Tracy E. Grim, Thousand Oaks, CA (US)

(73) Assignee: Ossur, hf, Reykjavik (IS)

( * ) Notice: Subject to any disclaimer, the term of this patent is extended or adjusted under 35 U.S.C. 154(b) by 110 days.

(21) Appl. No.: 11/112,101

(22) Filed: Apr. 21, 2005

(65) Prior Publication Data

US 2006/0237579 A1  Oct. 26, 2006

(51) Int. Cl.
*B65H 49/20* (2006.01)
(52) U.S. Cl. ................... 242/588.3; 206/409
(58) Field of Classification Search ........... 242/588, 242/588.3, 588.5; 206/389, 390, 409, 412, 206/438, 570, 588, 593, 594; 220/378, 795, 220/806, 849, 324, 326
See application file for complete search history.

(56) References Cited

U.S. PATENT DOCUMENTS

| | | | |
|---|---|---|---|
| 1,123,470 A | 1/1915 | Betten | |
| 1,135,110 A | 4/1915 | Hall | |
| 1,208,701 A | 12/1916 | Trenner | |
| 1,827,354 A | 10/1931 | Cooper | |
| 2,367,417 A | 1/1945 | Milem | |
| 2,646,877 A * | 7/1953 | Scholl | 206/409 |
| 3,298,580 A | 1/1967 | Lemer | |
| 4,027,795 A | 6/1977 | Rigden | |
| 4,244,493 A * | 1/1981 | Harrison | 206/409 |
| 4,249,658 A | 2/1981 | Ogura | |
| 4,382,510 A | 5/1983 | Gaffney | |
| 4,411,262 A | 10/1983 | von Bonin et al. | |
| 4,502,479 A | 3/1985 | Garwood et al. | |
| 4,505,387 A | 3/1985 | Seto | |
| 4,526,291 A * | 7/1985 | Margulies | 206/409 |
| 4,535,912 A * | 8/1985 | Bonk | 206/409 |
| 4,606,134 A * | 8/1986 | Flick | 206/409 |
| 4,658,959 A | 4/1987 | Inoue | |
| 4,662,516 A * | 5/1987 | Baker et al. | 206/363 |
| 4,770,299 A | 9/1988 | Parker | |
| 4,863,027 A * | 9/1989 | Yano | 206/390 |
| 4,869,046 A | 9/1989 | Parker | |
| 4,899,738 A | 2/1990 | Parker | |
| 5,003,970 A | 4/1991 | Parker et al. | |
| 5,133,980 A | 7/1992 | Ream et al. | |
| 5,238,137 A * | 8/1993 | Cornwall | 220/328 |
| 5,358,113 A | 10/1994 | Hellenbrand | |
| D370,728 S | 6/1996 | Edgar et al. | |
| 5,533,621 A | 7/1996 | Schoal, Jr. | |
| 5,607,387 A | 3/1997 | Martin et al. | |
| 5,641,062 A | 6/1997 | Burton et al. | |
| 5,704,480 A | 1/1998 | Scholz et al. | |

(Continued)

*Primary Examiner*—William A. Rivera
(74) *Attorney, Agent, or Firm*—Bacon & Thomas, PLLC (57) ABSTRACT

A dispenser box for medical bandages including orthopedic splints is described. The dispenser box includes at least one moisture impermeable container connected with a face plate containing a periphery gasket. The bandage exits through a slot in the face plate. A door is pivotally connected to and mechanically biased against the face plate. When the door is closed, a moisture resistant environment is maintained for the stored bandage materials.

19 Claims, 8 Drawing Sheets

U.S. PATENT DOCUMENTS

| | | |
|---|---|---|
| 5,711,493 A | 1/1998 | Harris et al. |
| 5,755,678 A | 5/1998 | Parker et al. |
| 5,782,786 A | 7/1998 | Tomaiuolo |
| 5,003,970 A | 7/1999 | Parker et al. |
| 5,981,823 A | 11/1999 | Turngren |
| 6,126,622 A | 10/2000 | Darcey et al. |
| 6,220,435 B1 * | 4/2001 | Nobile et al. ............... 206/409 |
| 6,341,691 B1 | 1/2002 | Voss |
| 6,719,710 B2 | 4/2004 | Darcey |
| 2003/0209557 A1 | 11/2003 | Taylor |
| 2005/0226795 A1 * | 10/2005 | Drummond et al. ........ 206/438 |

\* cited by examiner

DISPENSER BOX

FIELD OF THE INVENTION

The present invention relates to packaging and dispensing of medical bandages including, for example, medical dressings, tubular gauzes, and splints. More specifically, the present invention relates to packaging and dispensing of medical bandages stored from a supply within a container or dispenser.

BACKGROUND OF THE INVENTION

Medical bandages frequently are manufactured and distributed in rolls. Examples of these medical bandage rolls are tubular gauze and layered splints. Tubular gauze bandages are cylindrical bandages used to cover body appendages such as fingers, arms, and legs. Layered splint bandages are used in orthopedic casting and typically harden after exposure to moisture. These medical bandage rolls are very frequently used in hospitals, clinics, and physician offices. The bandage rolls may be packaged in a specially sealed bag or pouch. Furthermore, some of these bandage rolls are delivered in a pouch that further includes a disposable outer cardboard container or dispenser. Other bandage roll dispensers are reusable, and accept a disposable packaged roll of tubular gauze or splint.

Current dispensers have an opening in the front of the dispenser. Typically, a free end of the bandage passes through the opening in the dispenser, and a similar such opening in the pouch. One disadvantage of dispensers with front openings is that the free end of the bandage material may retract back into the pouch. The protective pouch must have a large enough opening to gain access to the free end. This results in exposure of the entire roll to atmospheric moisture when the pouch is widely opened in order to again grasp the free end.

Another object of medical bandage dispensers is to attempt to keep moisture out of the bandage material. This is especially important when the bandage material is an orthopedic splint that is sensitive to moisture. U.S. Pat. No. 4,411,262 (von Bonin, et al.) and U.S. Pat. No. 4,502,479 (Garwood, et al.) disclose an orthopedic splinting material, useful for orthopedic casting, and comprising a flexible fabric impregnated with a resin that hardens when exposed to water. This splinting material may be distributed as a bandage roll. Although an improvement over plaster of paris orthopedic splints which are heavy, and deteriorate if the patient gets the cast wet, moisture-curing resin splinting material does have a disadvantage. Whereas plaster of paris splints have a long shelf life, moisture-curing resin splints are extremely sensitive to the presence of any moisture. Even atmospheric moisture may activate the resin, hardening the stored splint material prior to use. Therefore this splinting material must be enclosed in moisture resistant packaging for storage until just prior to use. Once a package of such splinting bandage is opened, the entire roll must be used within a very short time to prevent premature curing.

U.S. Pat. No. 5,003,970 (Parker, et al.) attempts to address the problem of moisture entering stored resin splint bandages by providing an outer container and having an elongate product dispensing sleeve which is moisture proof and has a sealable opening. The Parker '970 dispenser, however, has several disadvantages. It is difficult to securely seal the end of the dispensing sleeve after cutting off a portion of the splint for use. One disclosed method of sealing the sleeve includes resealable zipper seals. In practical use, though, it is difficult to determine when these types of "zip-lock" seals have been closed moisture-tight. Also disclosed in the Parker '970 patent is a tape used to provide a seal, but repeated opening and closing of the tape adhesive is likely to weaken the adhesive seal over repeated use. Also disclosed is a clamp that may be used to seal the dispensing sleeve after the dispenser sleeve is opened. However, the clamp is prone to be misplaced or lost. Finally, heat sealing is impractical in a busy clinical setting.

Applying the seal in all of the prior art methods disclosed requires that the splint bandage not be present at the very end of the dispenser sleeve. Sealing requires that the end of the dispenser sleeve not have any intervening bandage in order to effect the seal. The seal may be applied, and the splint bandage maintained in a waterproof condition, only after the bandage is pushed back into the dispensing sleeve. The need to push bandage back up the dispensing sleeve, in order to effect a seal, is a significant disadvantage to the prior art devices. This makes it extremely difficult to grasp the free end of the splint bandage during subsequent uses and leads to increased time to seal the package up after each use.

SUMMARY OF THE INVENTION

Accordingly, the present invention is directed to overcoming some or all of the aforementioned disadvantages. The present invention in a preferred embodiment provides a dispenser box which keeps atmospheric exposure of the orthopedic splint bandage material contained therein to a minimum. The dispenser box should preferably be moisture resistant. A moisture resistant dispenser box will be advantageous for use with orthopedic splint flexible fabric impregnated with a resin because these splints will harden when exposed to moisture.

The present invention also provides a dispenser box that allows easy one-handed access to bandage materials. It is highly desirable for the dispenser box to permit both dispensing of bandage material, and opening and closing of the dispenser box, with one-handed operation.

In addition, the present invention prevents the medical bandage from retracting into the interior of the container. Retraction makes it difficult to find the free end of the bandage without opening up the entire packaging. Preferably, it should be easy to find the free end of the medical bandage without having to open up the entire packaging. It should also be easy to seal the dispenser box without having to push the free end of the medical bandage back into a sleeve. Preferably, after cutting off used bandage with scissors, the new free end need not be touched or manipulated when sealing the unused remaining portion of bandage material within the dispenser box.

In certain embodiments, the present invention provides a medical bandage storage device and dispenser, comprising at least one container including a moisture impervious material. A medical bandage having a free end is held within the container. The container has at least one aperture wherein the free end of the medical bandage passes therethrough. A face plate is disposed on said container, the face plate having a face slot that is substantially coextensive with the aperture such that the free end passes therethrough. A door having a periphery gasket is pivotally connected with the face plate and is mechanically biased against the face plate. There is a recess formed at least in one of the face plate and the door, and a chamber formed by the recess and the door holding the free end therein, wherein the periphery gasket blocks entry of moisture into the chamber.

In other embodiments, the invention provides a medical bandage dispenser box, comprising a substantially rigid exterior container, a roll of medical bandage having a free end, and a moisture resistant, collapsible interior container holding the roll and disposed within the exterior container, wherein the inner container includes at least one aperture for passage of the free end therethrough. A face plate is disposed on the inner container, wherein the face plate further includes a face slot that is in alignment with the aperture. A door is pivotally connected with the face plate beneath the face slot. A chamber is at least partially formed by closing the door against the face plate wherein the free end is located therein. A periphery gasket is disposed on at least one of the door and the face plate, wherein the gasket substantially prevents entry of moisture into the chamber.

In yet another embodiment, the invention provides a medical bandage dispenser box for storing a roll of medical bandage, comprising an exterior container having an upright lower portion and an angled upper portion, and an interior moisture resistant container substantially disposed within the exterior container. The inner container has at least one aperture for the dispensing of the medical bandage. A face plate covering the aperture is disposed on the angled upper portion of the exterior container, wherein the face plate includes a face slot leading into the inner container. A slot gasket is disposed at the face slot that is not moisture impervious. A door is pivotally joined to the face plate. A periphery gasket is disposed on at least one of the door and the face plate, wherein a moisture resistant seal is formed between the face plate and the door when the door is biased against and abutting the face plate. A recess is disposed in at least one of the door and the face plate, wherein a chamber is formed when the door is biased against and abutting the face plate. There is also a means for mechanically biasing the door against and abutting the face plate.

In still another aspect of the invention, a storage box is provided to hold and store the dispenser boxes together in an organized manner. The storage boxes may be supplemented with a non-skid surface on the bottom. The storage boxes are advantageous in organizing the dispenser boxes.

Further features and advantages of the present invention will become apparent to one of skill in the art in view of the Detailed Description of the Preferred Embodiments which follows, when considered together with the attached drawings and claims.

DETAILED DESCRIPTION OF THE PREFERRED EMBODIMENTS

Medical bandages include, for example, orthopedic layered splint material or tubular gauze. Tubular gauze bandages are cylindrical bandages used to cover body appendages such as fingers, arms, and legs. Layered splint bandages are used in orthopedic casting and typically harden after exposure to moisture. A common type of orthopedic splinting material, useful for orthopedic casting, comprises a flexible fabric impregnated with a resin that hardens when exposed to water. Resin impregnated bandages are very sensitive to moisture, even atmospheric moisture.

It is therefore advantageous to store these types of bandage supplies in a moisture and atmosphere resistant container between uses. Furthermore, it is well known that medical bandages come in a variety of widths in order to accommodate bandage application to various sizes of limbs and appendages. It is therefore advantageous for various embodiments of dispenser boxes to be made in a variety of sizes and shapes to accommodate the various widths and lengths of bandages and splints.

Figure 1:
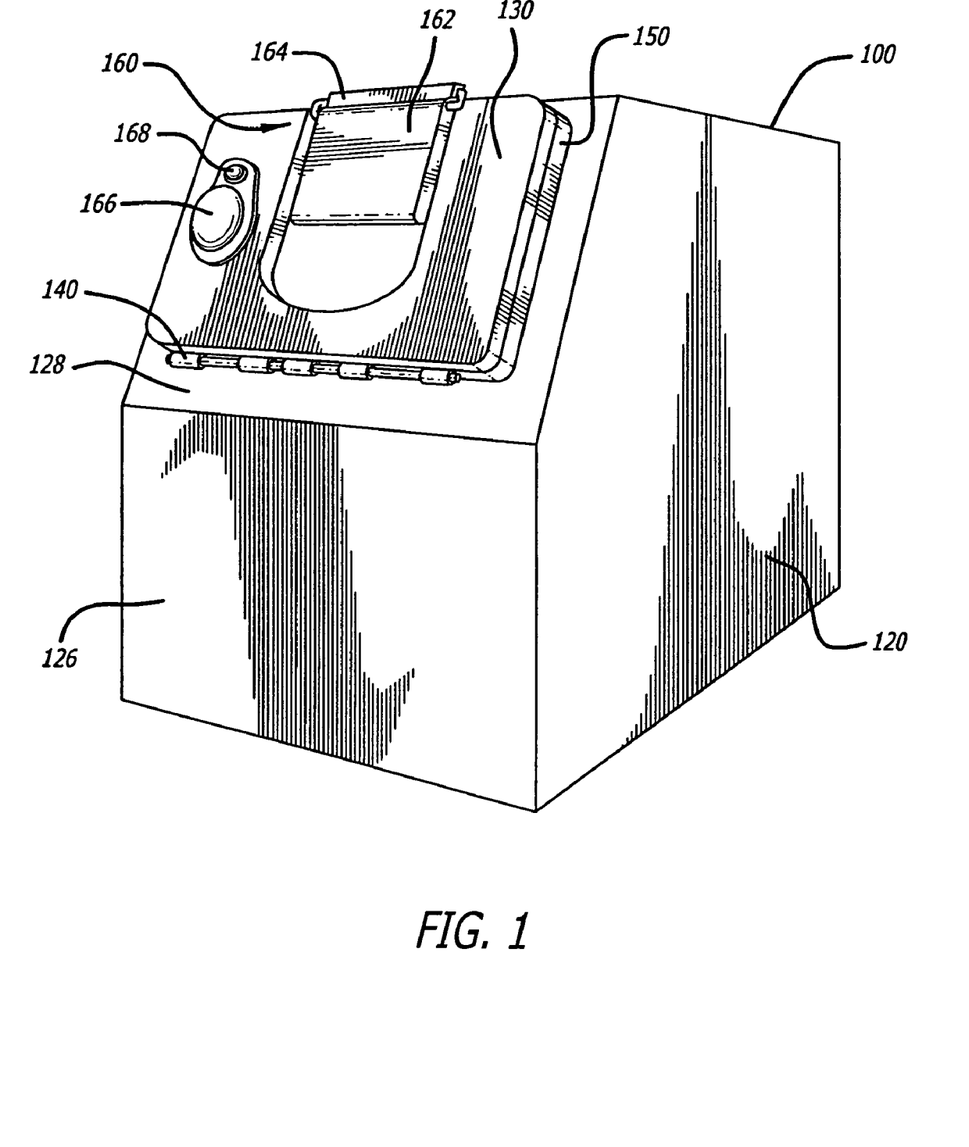
FIG. 1 is a perspective view of one embodiment of the dispenser box showing the door closed.

Referring first to FIG. 1, the present invention in its various embodiments is directed to a dispenser box 100 which includes a door 130 biased against a dispenser face plate 150. A moisture resistant seal is formed between the door 130 and the face plate 150, which prevents exposure of medical bandages to moisture in the atmosphere when the door 130 is closed. An embodiment of the dispenser box 100 of the present invention includes at least one container made of moisture resistant or moisture impervious material with a door 130 that seals out atmospheric moisture. In at least one preferred embodiment, the dispenser box 100 has a substantially rigid exterior container 120. The exterior container 120, in some embodiments, is made from cardboard, stainless steel, opaque plexiglass, transparent plexiglass, and/or glass filled polypropylene or like polymers.

The door assembly is located on a front side of the dispenser box 100. An edge of the door 130, preferably the lower edge, is pivotally connected with a corresponding lower edge of the dispenser face plate 150 by means of a hinge 140, whereby the door 130 may pivotally rotate between an open position and a closed position. It is further preferable to pivot the door 130 at the lower edge, as it is more ergonomic and permits unobstructed access to do so. However, it should be recognized that the door 130 could alternatively be hinged to open to either side, or upwardly. The door 130 is preferably made of an injection moldable plastic with a low moisture vapor transfer rate such as a polypropylene or the like. To increase the stiffness or rigidity of the door 130, additives may be included such as glass or talc. Alternatively, for further strength benefits, the door can be molded out of a nylon or other rigid plastic materials (which have a tendency to absorb moisture) and then coated with a more moisture impervious material such as polypropylene. One such process to achieve this effect is by co-injection molding.

The door 130 further has a mechanical door locking mechanism 160, that includes a latch 162, preferably located on the edge of the door 130 opposite the hinge 140, and a corresponding latch receiving member 164 connected upon the dispenser face plate 150. The locking mechanism 160 functions to mechanically bias and lock the door 130 in the closed position against the dispenser face plate 150, when the latch 162 engages the corresponding latch receiving member 164. The latch 162 and latch receiving member 164 provide an advantageous mechanical biasing mechanism that ensures a tight seal between the door 130 and the face plate 150. The locking mechanism 160 is preferably of the kind that provides one-handed intuitive functioning for easier use by the clinician. Alternative embodiments of the locking mechanism are described below.

Figure 2A:
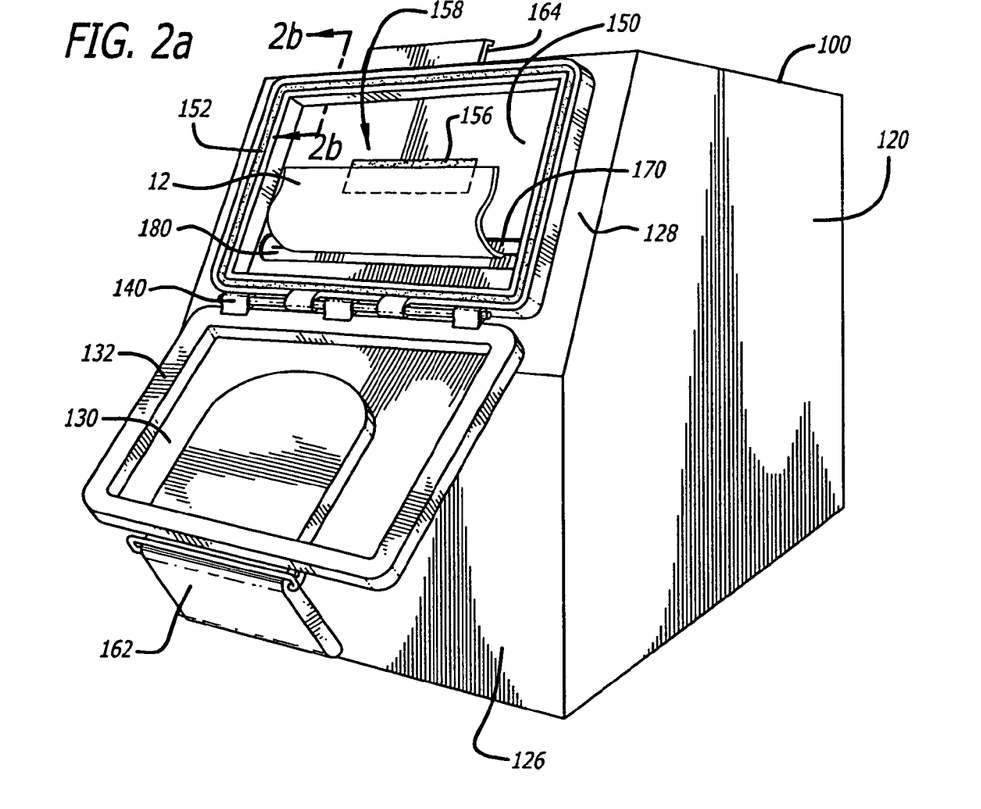
FIG. 2a is a perspective view of the dispenser box with the door open and showing medical bandage being held to the dispenser face plate by a hook fastener.

As shown in FIG. 2a, in one embodiment of the locking mechanism, the latch 162 includes a generally rectangular panel with a bent edge and a rectangular shaped ring hinged to the rectangular panel. The latch receiving member 164 in this embodiment includes a hook. The locking mechanism 160 locks the door in a closed position when the rectangular shaped ring loops over the hook shaped latch receiving member 164 formed in the face plate 150 or dispenser box 100. The latch 162 with its large panel and bent edge may further function as a handle to assist in opening the door 130, making it easer for the clinician to access the bandage.

Figure 7:
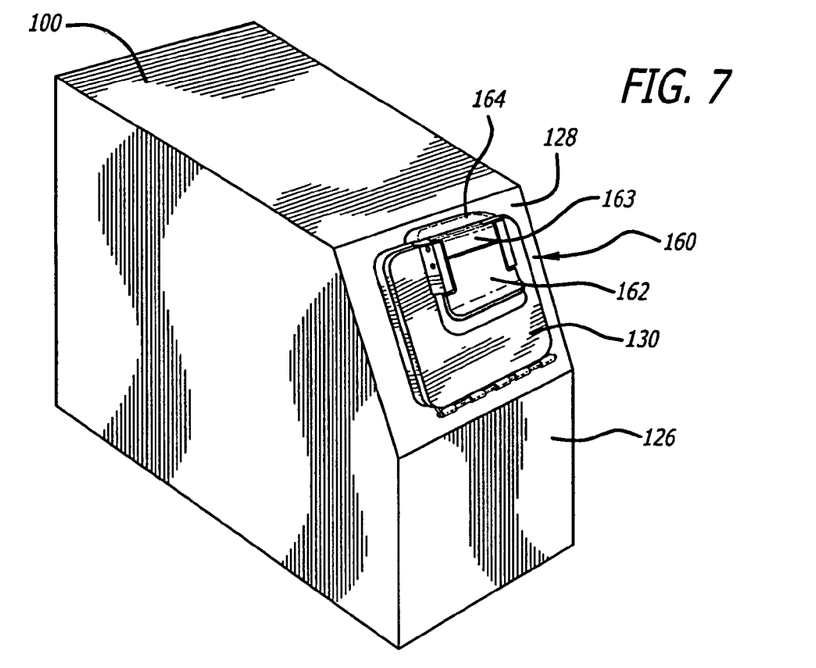
FIG. 7 is a perspective view of another embodiment of the dispenser showing another door locking mechanism.
Figure 8:
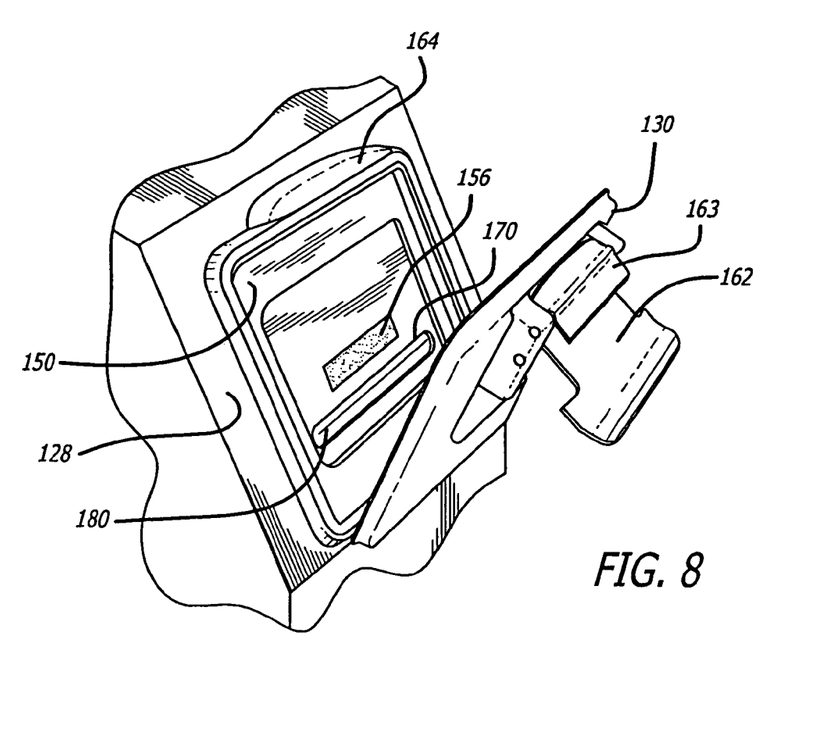
FIG. 8 is a perspective view the dispenser showing the door locking mechanism of FIG. 7 in an unlocked position.

Referring briefly now to FIG. 7 and FIG. 8, another embodiment of the locking mechanism is shown. This latch 162 includes a large generally rectangular panel, and further includes a pivoting pawl 163. The corresponding latch receiving member 164 includes an overhanging ledge, with a lip formed underneath. The pivoting pawl 163 rotates and is forced into locking engagement with the lip of the latch receiving member 164 as the generally rectangular panel is rotated parallel to the door 130. Likewise, the pivoting pawl 163 unlocks from the latch receiving member 164 as the generally rectangular panel is rotated away from the door 130. It is important that this type of latch contain a toggle feature. This ensures that the latch stays closed when the rectangular panel is in the closed position and will not accidentally open and compromise the moisture impervious seal without an intentional action by the user.

In each embodiment, the locking mechanism 160 is designed to provide an appropriate mechanical biasing or clamping force (approximately 1.5±0.5 lbs./linear in.) to assure a moisture tight seal between the door 130 and the gasket 152 located on the face plate 150. The mechanical biasing force generated between the latch 162 and latch receiving member 164 is greater than the magnetic attraction biasing force generated in a magnetic closure as disclosed in, for example, U.S. Pat. No. 5,704,480 (Scholz, et al.).

A large, mechanical, non-magnetic, biasing force is desired for achieving a moisture resistant or impermeable seal. In a preferred embodiment, the latch 162 is injection molded and made of a rigid plastic such as a glass filled polypropylene or glass filled nylon. These materials provide sufficient strength to the major components so that the latch 162 does not buckle, distort, or fail under repeatedly applied loads as well as minimizing fabrication costs.

When the door 130 is in a closed position, the bandage 10 is not visible. The door 130 may further bear a label as to the type and size of bandage 10 contained within the dispenser box 100. Also, the door 130 advantageously may be opened with one hand, the bandage 10 pulled out and cut for use, and the door 130 closed, all without the clinician touching the remaining unused bandage 10 that is stored inside the dispenser box 100. As long as an excessive amount is not left protruding, the remaining bandage 10 does not need to be pushed back in. The door 130 is closed and securely biased shut to obtain a moisture resistant seal.

Referring back now to FIG. 2a, the door 130 is shown in an open position. The dispenser face plate 150 includes an open face slot 170. At least one embodiment may include an optional pliant diaphragm or slot gasket 180 that is coextensive with the face slot 170. Specifically, the slot gasket 180 likewise has a horizontal opening that is coplanar and substantially coextensive with the face slot 170. The bandage therefore may pass through the opening in the slot gasket 180. The slot gasket 180 frictionally grips or holds the bandage 10 securely enough to prevent the free end 12 of the bandage 10 from accidentally retracting into the interior of the dispenser box 100. If the free end 12 of the bandage 10 were to retract into the interior of the dispenser box 100, it would be very inconvenient to retrieve. Notably, the slot gasket 180 is not intended to achieve a moisture resistant and/or air tight seal since the clamping force on the bandage 10 for such a seal may be too great for the bandage to pass through without using a great tugging force. Rather, the moisture resistant and/or air tight seal is provided between the door 130 and the periphery gasket 152. The slot gasket 180 may be injection molded directly into the dispenser face plate 150 in a two step process, or the slot gasket 180 may be molded separately and then connected, for example by adhesive, to the dispenser face plate 150.

In at least one embodiment, a hook fastener 156 is connected with the front of the face plate 150. Hook and loop fasteners of this type are well known in the art. The free end 12 of the bandage 10 may be curled upward against the hook fastener 156. The external layer of an orthopedic bandage 10 will adhere to the hook fastener 156, thereby preventing the free end 12 of the bandage 10 from retracting through the slot gasket 180, into the interior of the container. It is therefore not required for the slot gasket 180 to firmly grip the bandage 10. The free end 12 of the bandage 10 can be detached from the hook fastener 156 when the clinician wishes to dispense additional bandage 10.

The periphery of the dispenser face plate 150 preferably includes a periphery gasket 152, and the periphery of the door 130, preferably includes a periphery mating surface 132. The periphery gasket 152 and the periphery mating surface 132, when tightly abutting against each other, together form the moisture resistant seal as the door 130 is biased shut against the dispenser face plate 150. In some alternative embodiments, the periphery gasket 152 is disposed on the door 130 instead of the face plate 150, and the periphery mating surface 132 is disposed on the face plate 150. In yet other alternative embodiments, when two periphery gaskets are used (one on the face plate 150 and one on the door 130), the periphery mating surface 132 may be entirely omitted.

In at least one embodiment, the hinge 140 may include a spring (not shown) that further biases the door 130 against the dispenser face plate 150. This is advantageous in keeping the door 130 automatically closed between uses. In some embodiments, a catch (not shown) may be included that holds the door in an open position, counteracting the spring during dispensing of bandage. Various ways to include a biasing spring into a hinge 140 are well known in the art and need not be discussed in more detail herein.

Figure 2B:
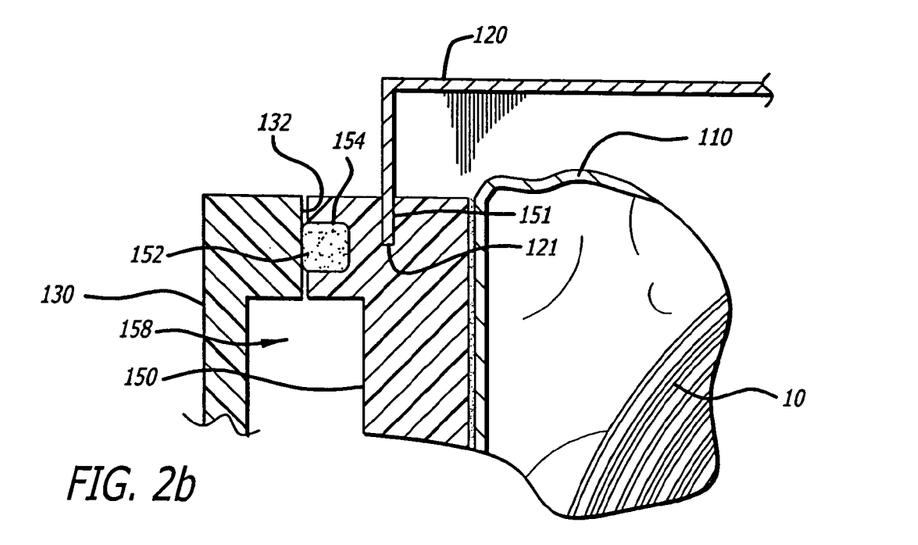
FIG. 2b is a vertical cross-sectional view through the front of the dispenser box showing the interior container within the exterior container and further demonstrating the periphery gasket seated within a channel in the dispenser face plate.

Referring now to the cross-sectional view of FIG. 2*b* taken along line 2*b*-2*b* of FIG. 2*a*, in at least one preferred embodiment, the dispenser box 100 has an interior container 110 made of moisture impervious material inserted within an optional exterior container 120. The interior container 110 in some embodiments is collapsible and further includes one or more gussets. In alternative embodiments, the interior container 110 and the exterior container 120 may be combined into one container.

As shown in FIGS. 2*a* and 2*b*, the periphery gasket 152 is preferably seated within an optional channel 154 that is designed to securely accept the periphery gasket 152. The periphery gasket 152 preferably has a low durometer, which reduces the necessary clamping force of the locking mechanism 160 while still providing an adequate seal for prevention of moisture and/or air from entering around the closed door 130. In an alternative embodiment (not shown), the channel 154 and periphery gasket 152 may be formed into the door 130 instead of the dispenser face plate 150. In another alternative embodiment, the channel and gasket are omitted and a ridge or rib integral with and circumscribing the periphery of the door 130 and/or face plate 150 would serve as the seal or moisture barrier.

Figure 10A:
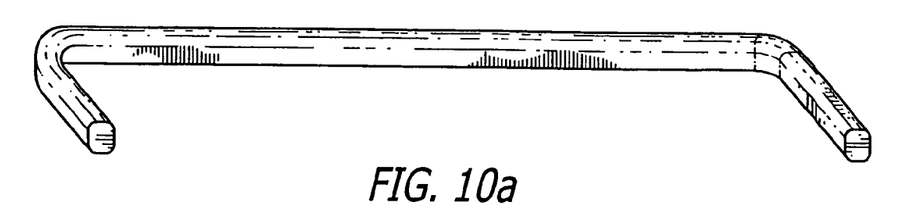
FIGS. 10a, 10b, and 10c are partial perspective views of alternative embodiment peripheral gaskets.
Figure 10B:
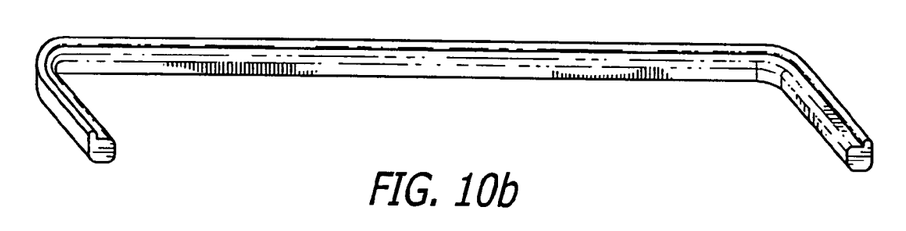
Figure 10C:
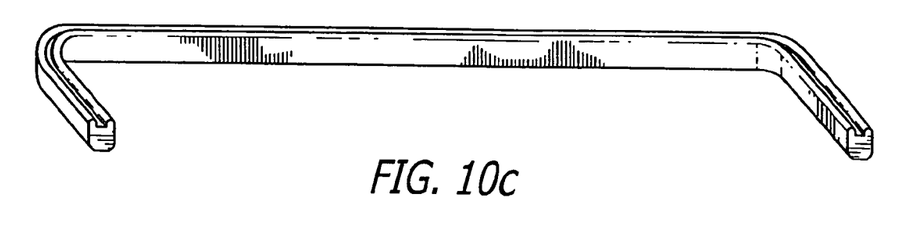

Preferably the periphery gasket 152 is made from a thermoplastic elastomer such as DYNAFLEX G6713-0007 from KRATON Polymers in Houston, Tex., or STARPRENE 202-15. Of course, rubber, or any polymer of low durometer such as polyurethane, polyethylene, or the like can be used. The periphery gasket 152 is made from a single strand of material, or it can be installed in discrete sections. As seen in FIGS. 2*a* and 2*b*, the periphery gasket 152 has a generally rectangular annulus shape with a square cross-section. Naturally, the overall annulus configuration can change to match the general shape of the door 130 and/or the face plate 150. Further, other cross-sectional shapes for the periphery gasket 152 are contemplated. FIGS. 10*a*-10*c* are partial perspective views of alternative embodiment periphery gaskets having a rectangular, an angled, and a channel cross-sectional shape, respectively. The optional single rib in FIG. 10*b* and double rib in FIG. 10*c* further improve the sealing effect of the gasket by increasing pressure along the smaller, raised contact area. The rib may have a semicircular cross-sectional shape as shown or may have a rectangular or triangular cross-section. In sum, one net benefit of all of the foregoing periphery gasket structures is to decrease the clamping force necessary to seal out atmospheric moisture thereby maximizing the functional reliability and ease-of-use of the mechanical door locking mechanism.

In at least one embodiment, a recess may be molded into the door 130 or dispenser face plate 150, or both, thereby forming a chamber 158. The chamber 158 thus formed between the door 130 and the face plate 150 provides an enlarged space that further accommodates storage of the free end 12 of the bandage 10. The chamber 158 is defined by a barrier circumscribed area within which the inner surface of the door 130 does not directly contact the surface of the face plate 150 or periphery gasket 152. The thickness of the space between the inner surface of the door 130 and surface of the face plate 150 defining the chamber depth is, for example, in the range of about ⅛ inch to 2 inches, and all dimensions therebetween. It is advantageous while providing a chamber 158 not to make this space larger than needed to accommodate the bandage 10, thereby allowing as little moisture as possible to come in contact with the bandage 10. Indeed, the chamber depth may be less than the thickness of the bandage 10 and more room is created by a slight bowing in the door 130. In such an embodiment, the circumscribing periphery of the door 130 still seats tightly against the face plate 150 surface or preferably against the periphery gasket 152.

The chamber 158 may be rectangular or polygonal in shape and have a rather squared off depth as shown in FIGS. 2*a* and 2*b*. Alternatively, the chamber 158 may have a more rounded shape with a concave bottom, or any combination of the foregoing.

The chamber 158 advantageously facilitates a secure, moisture resistant and/or air tight closure of the door 130 against the periphery gasket 152, by preventing the thickness of the free end 12 of the bandage 10 from obstructing complete closure of the door 130. To be sure, the door 130 will not form a good seal against the periphery gasket 152 if a thick bandage obstructs the door 130 from tightly closing against the gasket 152.

Furthermore, the chamber 158 is very advantageous in decreasing stress on the hinge 140 and the latch 162 when using the dispenser box 100 with thick orthopedic splints. Lacking a chamber 158, that is if the inner surface of the door 130 were flat and directly abutting a similarly flat surface of the face plate 150, the free end 12 of a thick orthopedic splint located between the door 130 and the face plate 150 would exert a strong outward force upon the door 130 and related structures. More likely, without the chamber 158, the door 130 would be held open by the thickness of the bandage 10 making it impossible to create a moisture tight seal. By including a chamber 158 in the exemplary embodiment, the splint bandage 10 is retained between the door 130 and the face plate 150 without the bandage 10 exerting any or very little force upon the door 130. Stresses upon the door 130, face plate 150, hinge 140, and locking mechanism 160 are thereby minimized by the inclusion of the chamber 158. The depth of the chamber 158 can be very minimal and varied in different embodiments to assist in the storage of various thicknesses of bandages 10. The chamber 158 is particularly advantageous when the dispenser box 100 is used with thick orthopedic splint material. Furthermore, the chamber 158 supplies a space for the addition of a desiccant, thereby having a further advantage of attracting trapped moisture away from orthopedic splints and medical bandages. The chamber 158 has the further advantage of allowing the user to leave the leading portion of the splint exposed and accessible for future uses through a small slit-like opening. This eliminates the need for a large opening to access the end of the splint which results in exposure of large amounts, or possibly the entire splint, to moisture.

Referring back again to FIG. 1, in at least one embodiment of the invention, a vacuum pumping mechanism 166, for example, a bulb or hand pump is included on the dispenser box 100, for example, on the door 130. (This only works if there is no interior container 110.) The door 130 may be difficult to open if there is negative pressure inside the dispenser box 100. Therefore, in some embodiments it is advantageous to further include a release valve 168 for relieving the negative pressure. The pump mechanism 166 communicates with the air that may enter around the supply of medical bandage 10 positioned within the interior container 110. In one embodiment, the pump 166 may be a rubber bulb that has a one-way valve at an inlet to the plenum and a one-way valve at the outlet to the plenum. Air is drawn in one direction out of the interior space into the plenum and conveyed out into the external atmosphere as the bulb is repeatedly squeezed and released. Accordingly, the pump 166 functions to remove the excess air and moisture from the inside of the interior container 110 and/or from the space between the dispenser face plate 150 and the closed door 130. After the door 130 has been securely closed, the vacuum pumping mechanism 166 is used to withdraw as much of the remaining air as possible from within the interior container 110 and more specifically from around the stored medical bandage supply. This is beneficial in preventing premature hardening of the splint material remaining within the interior container 100 from exposure to atmospheric moisture that may have entered during the dispensing of the bandage 10. The vacuum pumping mechanism 166 is also beneficial in securing the door 130 tightly shut.

Figure 3:
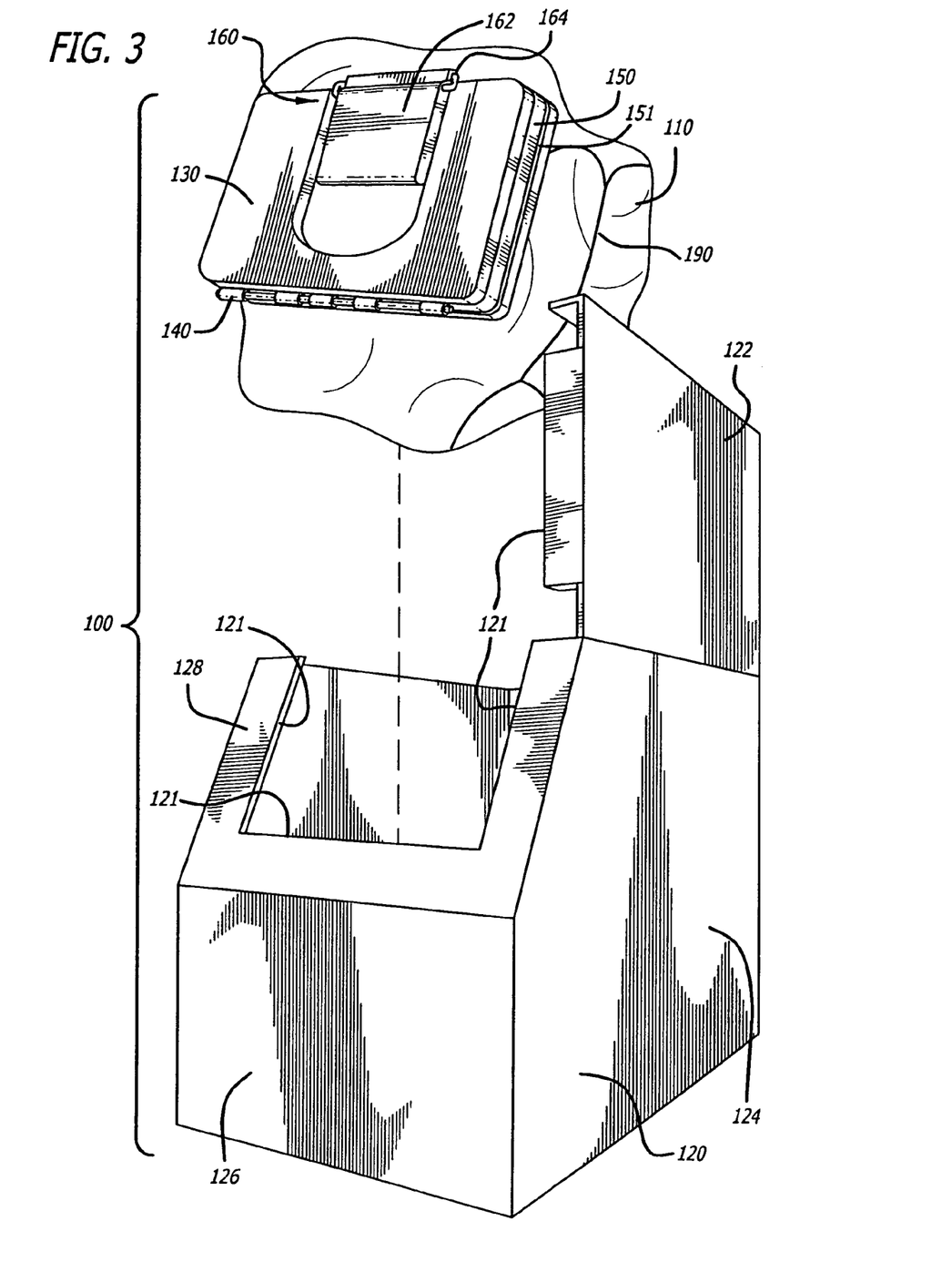
FIG. 3 is an exploded perspective view of the dispenser box showing a gusseted interior container with face plate removed from within an exterior container.

Referring now to FIG. 3, in at least one embodiment, the interior container 110 is a gusseted foil pouch 190. The interior container 110 is preferably collapsible, thereby minimizing the retained air therein. The interior container 110 is disposed within the exterior container 120. The exterior container 120 is preferably substantially rigid. A supply of medical bandage material (not shown), for example orthopedic splint roll, is located inside the gusseted foil pouch 190. The gusseted foil pouch 190 may, for example, in some embodiments have a two-panel design. The front side of the gusseted foil pouch 190 is connected in a moisture-tight fashion against the back of the dispenser face plate 150, for example by an adhesive.

An aperture cut in the front of the gusseted foil pouch 190, that is preferably substantially coextensive with the slot gasket 180 of the dispenser face plate 150 permits passage of the medical bandage from the inside of the interior container 110 out through the slot gasket 180. Again, the slot gasket 180 is designed to grip the bandage but does not provide the moisture resistant seal. The moisture resistant seal is instead provided between the door 130 and the face plate 150.

In at least one embodiment, the interior container 110 is inserted within the exterior container 120. This permits the interior container 110 to be disposable for use with a re-usable exterior container 120. The face plate 150 has a peripheral side wall groove 151 which interlocks with the peripheral edges 121 of an opening in the exterior container 120, thereby connecting the face plate to the exterior container 120. The groove 151 in the face plate 150, thereby slides onto and connects with the exterior container 120 in a tongue and groove fashion. The exterior container 120 gives further support and protection to the interior container 110.

The exterior container 120, in at least one embodiment, may be made of an inexpensive cardboard or plastic and therefore be disposable. Additional tabs and flaps may be added to the cardboard box for more strength. The disposable exterior container 120 may be shipped by the manufacturer with the interior container 110 pre-inserted in place. For example, the dispenser box 100 could be manufactured as a unitary disposable construct. Alternatively, a preassembled dispenser box 100 can include a re-usable exterior container 120 and a disposable interior container 110. For example, in some embodiments, the exterior container 120 may be made from a more permanent material, for example stainless steel or a rigid polymer. Furthermore, in some embodiments, the disposable interior containers 110 may be shipped separately, and thereafter inserted into a permanent and/or reusable exterior container 120 by the user. The interior container 110 may be removed from the exterior container 120 after all of the bandage 10 has been used, and a new interior container 110 with a fresh supply of bandages inserted into the exterior container 120.

In one preferred embodiment, at least one first panel 122 of the exterior container 120 is hingedly connected with at least one second panel 124 of the exterior container 120. The first panel 122 swings open, allowing access to the inside of the exterior container 120, and further allowing insertion of the interior container 110. The front side of the exterior container 120, in at least one embodiment, comprises an angled upper portion 128, and a substantially vertical lower portion 126. The angled upper portion 128 has an opening to receive the dispenser face plate 150 and connected door 130 securely therein. The peripheral edges 121 of the angled upper portion 128 join with the groove 151 of the face plate 150. The face plate 150 is secured inside the exterior container 120 when the first panel 122 is pivoted into a closed position, whereby the peripheral edge 121 of the first panel 122 is inserted into the groove 151 at the top of the face plate 150. Alternatively, clips, snaps, adhesives, or fasteners, for example, could hold the dispenser face plate 150 to the exterior container 120. Still other ways of seating the dispenser face plate 150 to the exterior container 120 will be recognized by those in the art.

The angled upper portion 128 permits the dispenser face plate 150 to sit at a rearwards slant. This angle of the dispenser face plate 150 is advantageous in providing a much more ergonomic method to dispense splint bandage. The angled upper portion 128 of the dispenser has the further advantage of allowing a splint roll to unroll and/or unfold more easily within the interior container 110.

Figure 4:
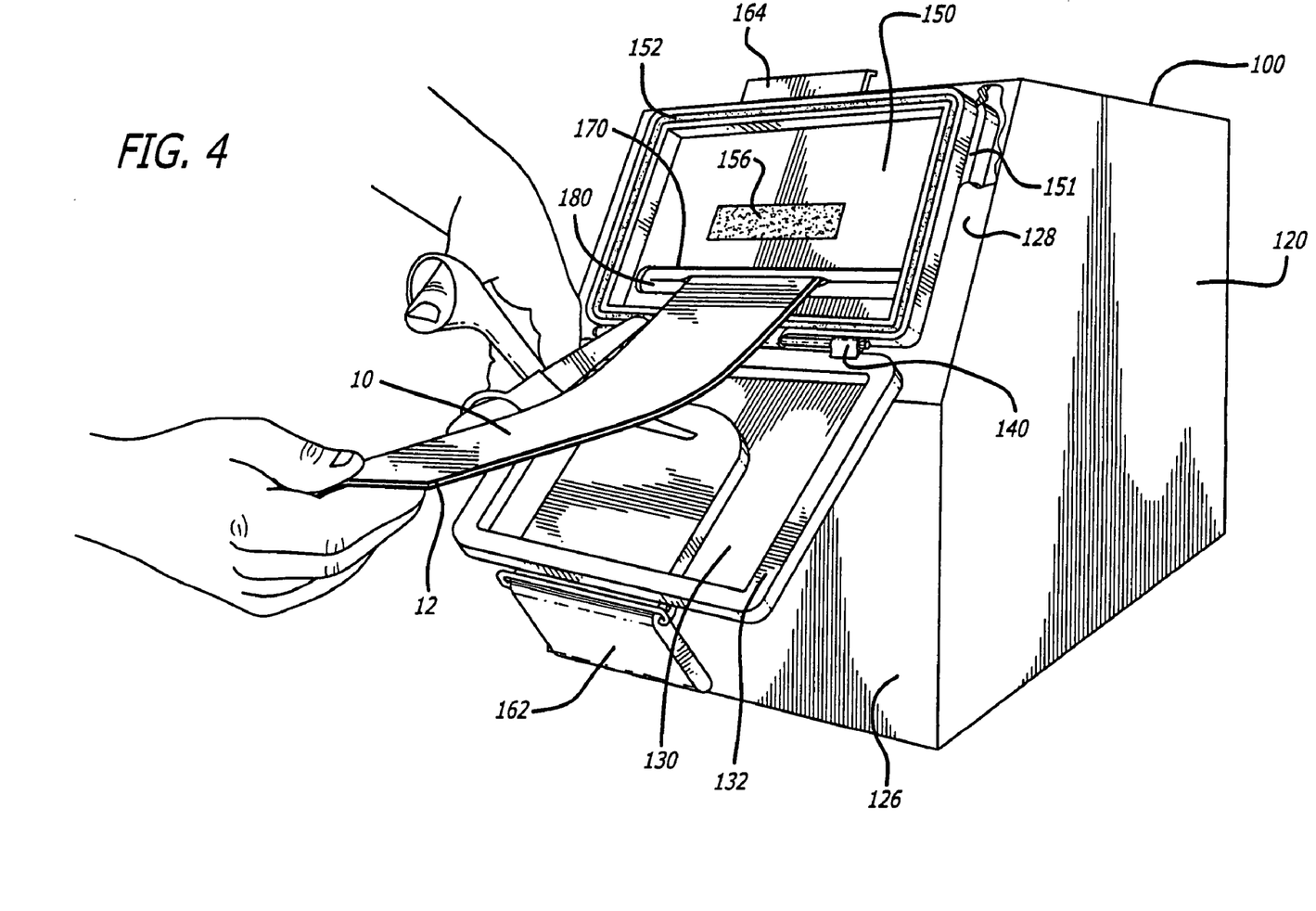
FIG. 4 is a perspective view of the dispenser box illustrating the door open with dispensed medical bandage about to be cut by scissors, and further including a fragmentary cut out showing the groove in the side of the face plate.

Referring now to FIG. 4, the free end 12 of the medical bandage 10 is dispensed from a supply of medical bandage material residing inside the interior container 110. The supply of bandages may be, for example, stored in the form of a roll or in a folded configuration. The medical bandage 10 is dispensed by the clinician grabbing the free end 12 of the medical bandage 10 and pulling additional bandage 10 from the supply within the interior container 110. The desired amount of medical bandage 10 may then be cut off by a cutting instrument, for example bandage scissors. In alternative embodiments, a cutting instrument, for example a sliding blade or guillotine blade, is incorporated into the dispenser box 100. As mentioned above, the slot gasket 180 aids in holding the bandage 10 and preventing the free end 12 of the bandage 10 from slipping back into the interior container 110. Furthermore, the free end 12 of medical bandage 10 is conveniently securable to the hook fastener 156 between uses and during shipping, which further ensures that the free end 12 does not retract back into the interior container 110.

After cutting of the bandage 10, approximately one to three inches of new free end 12 of bandage 10 is allowed to remain outside of the slot gasket 180 and is secured to the hook fastener 156. The dispenser door 130 may then be closed, securely retaining the free end 12 of bandage 10 between the door 130 and the dispenser face plate 150 for subsequent usage. The door 130 is then biased shut to create moisture resistant storage for the remainder of the medical bandage 10.

Figures 5, 6A, 6B:
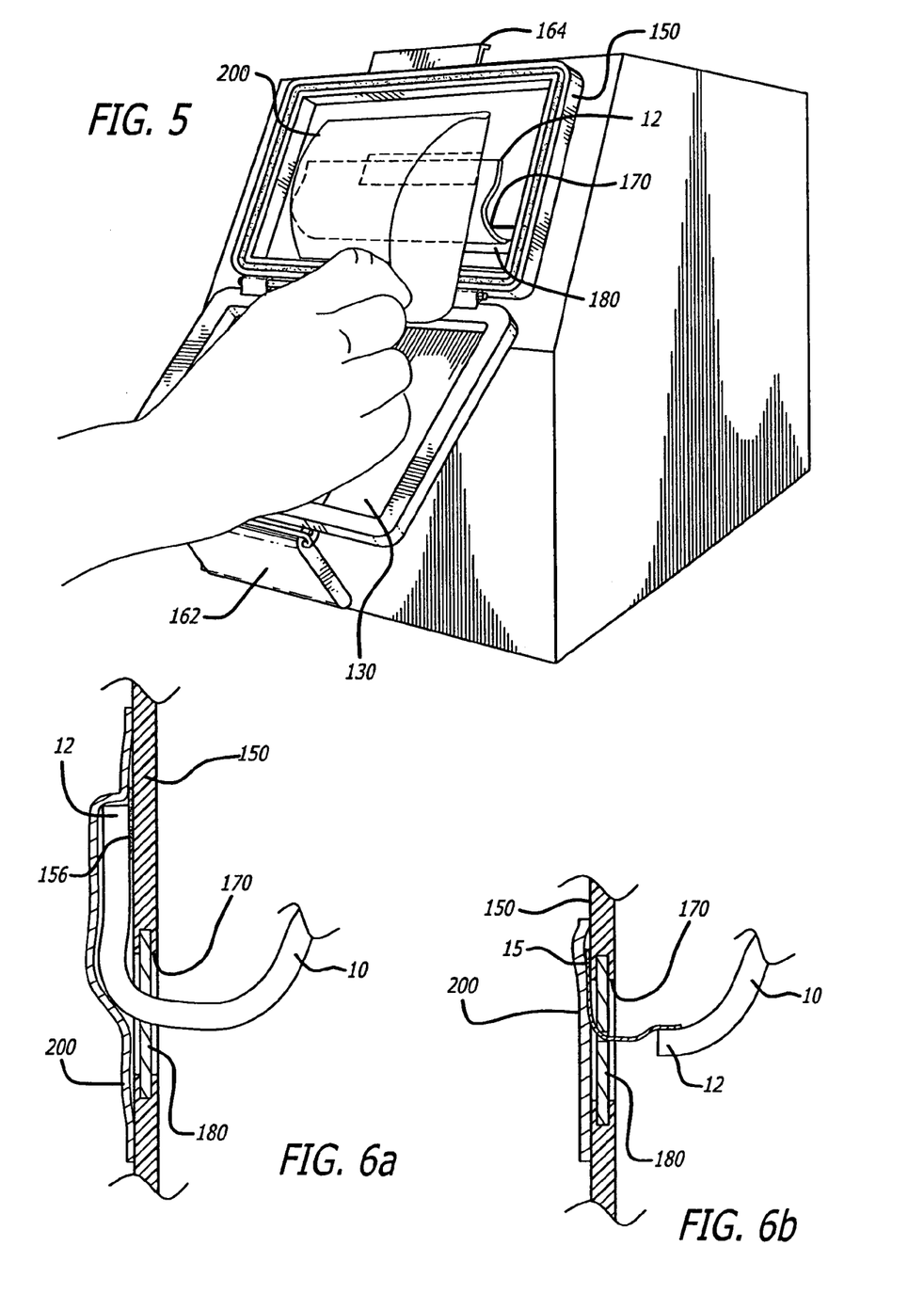
FIG. 5 is a perspective view of the dispenser box with the door open and demonstrating the removal of a slot seal from the dispenser face plate, thereby exposing the free end of the medical bandage coming through the slot gasket and attached to the hook fastener.
FIG. 6a is a cross-sectional view of the dispenser box further illustrating the relationship of the slot seal, slot gasket, hook fastener, and bandage.
FIG. 6b is a cross-sectional view of the dispenser box showing a starter tab, on the free end of a medical bandage, passing through the slot gasket.

As illustrated in FIG. 5, in at least one embodiment, a slot seal 200 is adhered to the outside of the face plate 150 prior to shipping. As shown in FIG. 6a, the slot seal 200 in at least one embodiment completely covers the bandage 10, the hook fastener 156, the face slot 170 and the slot gasket 180. The slot seal 200, which is moisture resistant thereby prevents moisture from entering into the interior container 110, and hardening the bandage 10, during shipment and storage. The slot seal 200 may be made from, for example, a moisture resistant foil sticker that is removably connected to the front of the dispenser face plate 150 by adhesives, ultrasonics, or other techniques known in the art. Furthermore, as shown in FIG. 6b, in at least one embodiment a tab 15 is used to connect the free end 12 of the medical bandage 10 with the back of the slot seal 200. Therefore, as the slot seal 200 is removed, the initial free end 12 of medical bandage 10 is pulled through the slot gasket 180 from the interior container 110. The slot seal 200 is disposed of after the free end 12 of the bandage 10 is delivered through the slot gasket 180. The free end 12 of the bandage 10 may then be secured to the hook fastener 156.

Figure 9:
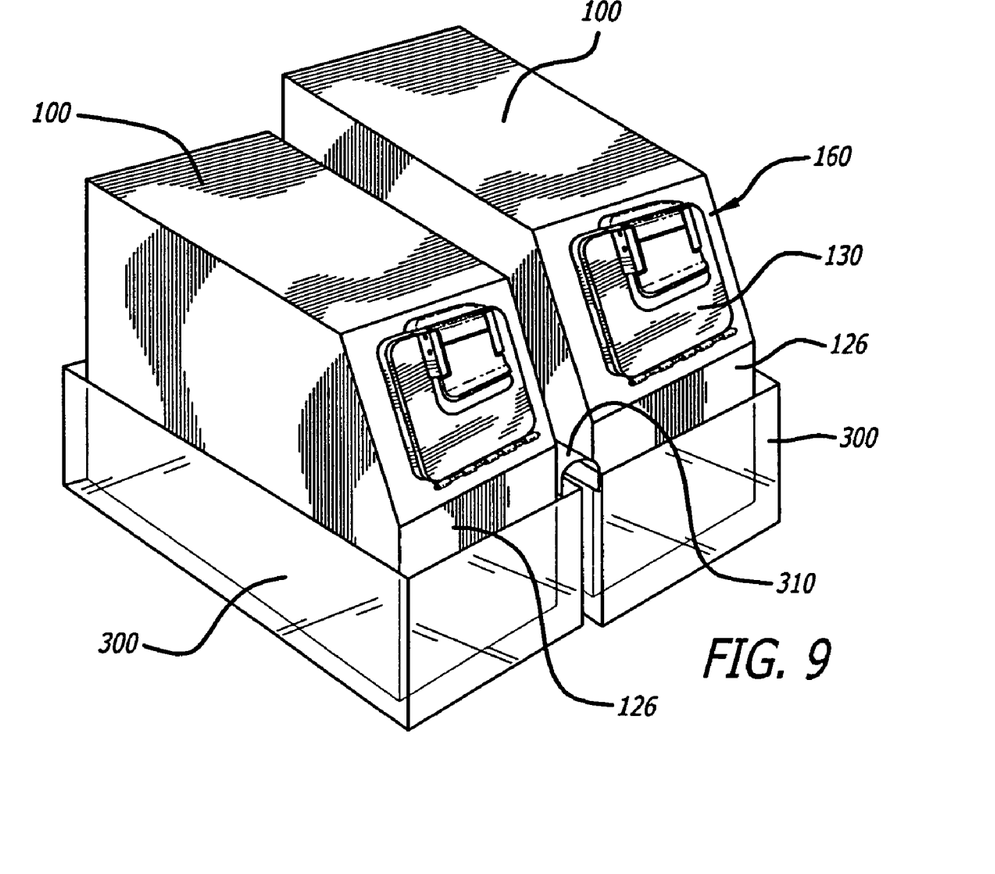
FIG. 9 is a perspective view of dispensers within storage box housings.

Referring now to FIG. 9, yet another aspect of the invention is a storage box housing 300 that accepts at least one dispenser box 100. The storage box housing 300 may be made from, for example, Plexiglas. The storage box housing 300 is a rectangular box, slightly larger in dimension than the length and width of a dispenser box 100. The bottom of the exterior container 120 of the dispenser box 100 slides into the top of the storage box housing 300. In addition, the bottom of the storage box housings 300 may be fitted with rubber foot pads, slip resistant strips, or footings in order to help prevent sliding of the storage box housings 300 and dispensers 100 on a counter top. The storage box housings 300 thus help to prevent sliding of the exterior container 120 when bandage 10 is being dispensed.

The height of the storage box housing 300 is sufficient to retain the dispenser box 100 within, however no higher than the vertical lower portion 126 of the exterior container 120. In other words, the height of the storage box housing 300 should not impede the free opening of the door 130 of the dispenser box 100. The storage box housing 300 may, in some embodiments, be made of a transparent plastic that will allow artwork on the dispenser box 100 to show through. Various storage box housings 300 may be made in different sizes in order to secure the various sizes of dispenser boxes 100 inside. Multiple storage box housings 300 may be joined to one another, for example by clips 310, or interlocking joints. This allows the clinician to conveniently organize the various sizes and types of bandages and splints.

Although the invention has been described for the purpose of dispensing medical bandage, the device is not restricted to use within health care. The dispenser box is suitable for the moisture resistant storage and dispensing of any long strip-like materials supplied in rolls. Therefore, other industries may find the invention beneficial. For example, the dispenser box may also be useful in construction and manufacturing.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

What is claimed is:

1. A medical bandage storage device and dispenser, comprising:
   at least one container including a moisture impermeable material;
   a medical bandage having a free end held within the container;
   the container having at least one aperture wherein the free end of the medical bandage passes therethrough;
   a face plate disposed on said container and having a face slot that is in communication with and substantially coextensive with the aperture such that the free end of the medical bandage passes therethrough;
   a door pivotally connected with the face plate and mechanically biased against the face plate;
   a recess formed at least in one of the face plate and the door;
   a periphery gasket extending outwardly from the face plate, the periphery gasket located between the face plate and the door; and
   a chamber formed by the recess and the door holding the free end of the medical bandage therein, wherein the periphery gasket blocks entry of moisture into the chamber by forming a seal between the door and the face plate.

2. The medical bandage storage device and dispenser as in claim 1, further comprising a door locking mechanism biasing the door closed, a slot gasket disposed coplanar and within the face slot, wherein the slot gasket is further aligned substantially coplanar with and substantially coextensive with the aperture.

3. The medical bandage storage device and dispenser as in claim 1, wherein the container further comprises a substantially vertical lower portion and a substantially angled upper portion, and wherein the face plate is disposed on the substantially angled upper portion.

4. The medical bandage storage device and dispenser as in claim 1, wherein the periphery gasket is secured within a channel in the face plate.

5. The medical bandage storage device and dispenser as in claim 1, wherein the door is biased against the face plate by a spring.

6. A medical bandage dispenser box for containing a medical bandage roll having a free end, comprising:
   a substantially rigid exterior container;
   a moisture impermeable, collapsible interior container configured for holding a medical bandage roll, wherein the inner container includes at least one aperture configured for passage of a free end of a medical bandage roll therethrough;
   a face plate disposed on the inner container, wherein the face plate further includes a face slot that is in communication with the aperture;
   a door pivotally connected with the face plate beneath the face slot;
   a chamber at least partially formed by closing the door against the face plate wherein the free end is at least partially located therein; and
   a periphery gasket extending from at least one of the door and the face plate so as to be located between the door and the face plate, wherein the gasket substantially prevents entry of moisture into the chamber by forming a seal between the door and the face plate.

7. The medical bandage dispenser box as in claim 6, wherein the dispenser box includes a means for mechanically biasing the door into the face plate.

8. The medical bandage dispenser box as in claim 7, wherein the means for mechanically biasing the door against the periphery gasket includes a latch disposed on the door and a latch receiving member disposed on the face plate.

9. The medical bandage dispenser box as in claim 6, wherein the periphery gasket engages a periphery mating surface connected with the door.

10. The medical bandage dispenser box as in claim 6, wherein the exterior container includes at least one of cardboard, stainless steel, opaque plexiglass, transparent plexiglass, and glass filled polypropylene.

11. The medical bandage dispenser box as in claim 6, wherein the box includes a slot seal covering the face slot and the free end of the bandage prior to the first use.

12. The medical bandage dispenser box as in claim 6, wherein the interior container includes a gusset.

13. A medical bandage dispenser box for storing and dispensing a roll of medical bandage, comprising:
   an exterior container having an upright lower portion and an angled upper portion;
   a moisture impermeable interior container substantially disposed within the extenor container;
   the inner container having at least one aperture for the dispensing of the medical bandage;
   a face plate disposed on the angled upper portion of the exterior container, wherein the face plate includes a face slot leading into the inner container;
   a slot gasket disposed at the face slot that is not moisture impervious;
   a door pivotally joined to the face plate;
   a periphery gasket disposed on at least one of the door and the face plate, wherein a moisture resistant seal is formed between the door and the periphery gasket when the door is biased against and abutting the face plate;
   a recess in at least one of the door and the face plate, wherein a chamber is formed when the door is biased against and abutting the face plate; and
   a means for mechanically biasing the door against the face plate.

14. The medical bandage dispenser box as in claim 13, further comprising a slot seal.

15. The medical bandage dispenser box as in claim 13, further comprising a means for removal of ambient air from within the inner container.

16. The medical bandage dispenser box as in claim 13, further comprising a storage box housing.

17. The medical bandage dispenser box as in claim 13, further comprising a desiccant disposed within the inner container.

18. The medical bandage dispenser box as in claim 13, wherein the periphery gasket includes at least one rib.

19. The medical bandage dispenser box as in claim 13, wherein the periphery gasket includes at least one of a square, rectangular, angle, and channel cross-sectional shape.

* * * * *